(12) United States Patent
Link et al.

(10) Patent No.: US 11,357,630 B2
(45) Date of Patent: Jun. 14, 2022

(54) CONNECTING SLEEVE FOR ANCHORING SHAFTS OF TWO OPPOSITELY ARRANGED PROSTHESES

(71) Applicant: Waldemar Link GmbH & Co. KG, Hamburg (DE)

(72) Inventors: Helmut D. Link, Hamburg (DE); Udo Borchers, Norderstedt (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 0 days.

(21) Appl. No.: 16/497,728

(22) PCT Filed: Mar. 29, 2018

(86) PCT No.: PCT/DE2018/100291
§ 371 (c)(1),
(2) Date: Sep. 25, 2019

(87) PCT Pub. No.: WO2018/177481
PCT Pub. Date: Oct. 4, 2018

(65) Prior Publication Data
US 2020/0146828 A1 May 14, 2020

(30) Foreign Application Priority Data
Mar. 31, 2017 (EP) ..................................... 17164128

(51) Int. Cl.
*A61F 2/28* (2006.01)
*A61F 2/30* (2006.01)

(52) U.S. Cl.
CPC ........ *A61F 2/28* (2013.01); *A61F 2002/2825* (2013.01); *A61F 2002/2853* (2013.01);
(Continued)

(58) Field of Classification Search
CPC .. A61F 2002/30196; A61F 2002/30329; A61F 2/28; A61F 2002/2825;
(Continued)

(56) References Cited

U.S. PATENT DOCUMENTS 4,011,602 A * 3/1977 Rybicki ................ A61F 2/3662
623/23.76
4,404,691 A * 9/1983 Buning ..................... A61F 2/32
623/20.15
(Continued)

FOREIGN PATENT DOCUMENTS

DE 20 2004 019 264 4/2006
EP 1 639 963 A1 3/2006
(Continued)

OTHER PUBLICATIONS

International Search Report and Written Opinion dated Aug. 2, 2018 in corresponding International Application No. PCT/DE2018/100291.
(Continued)

*Primary Examiner* — Yashita Sharma
*Assistant Examiner* — Melissa A Hoban
(74) *Attorney, Agent, or Firm* — Chiesa Shahinian & Giantomasi

(57) ABSTRACT

The invention relates to a connecting sleeve for anchoring shafts of two oppositely arranged prostheses, preferably on an elongate bone such as a femur or humerus. The reinforcing sleeve comprises two receiving bushes (1, 2) for one prosthesis shaft each and comprises a separable coupling region (3) arranged therebetween for connection in such a manner as to resist shear forces and rotation. According to the invention, each receiving bush (1, 2) has, on the side thereof facing the coupling region, one fork (31, 32) of a pair of forks that interact with each other, and a fitting block (4)
(Continued)

is arranged on a base of the fork, the lateral surfaces (44) of which fitting block have a distance that corresponds to an inner width of the fork, and the lateral surfaces (44) are designed to contact flanks of the fork in a planar manner, at least one fastening screw (5) being arranged transversely through the fork. The fork connection is simpler to produce than the known wedge connection and yet is sufficiently robust. Unlike in the case of the wedge connection, an exact fit is not required; a clearance fit between the fork (31, 32) and the fitting block (4) is sufficient in principle, excessive play being eliminated by means of the fastening screw (5).

10 Claims, 3 Drawing Sheets

(52) U.S. Cl.
CPC ............... *A61F 2002/30235* (2013.01); *A61F 2002/30331* (2013.01); *A61F 2002/30433* (2013.01); *A61F 2002/30604* (2013.01)

(58) Field of Classification Search
CPC .... A61F 2002/2853; A61F 2002/30235; A61F 2002/30331; A61F 2002/30433; A61F 2002/30604; A61F 2/30734; A61F 2/36; A61F 2/3804; A61F 2/4059; A61F 2002/30224; A61F 2002/30385; A61F 2002/30507; A61F 2002/3674; A61F 2/30721; A61F 2/3662; A61F 2/3859; A61F 2/30739; A61B 17/72; A61B 17/744
See application file for complete search history.

(56) References Cited

U.S. PATENT DOCUMENTS

| | | | | |
|---|---|---|---|---|
| 4,640,271 A | * | 2/1987 | Lower | A61B 17/8685 606/105 |
| 4,805,607 A | * | 2/1989 | Engelhardt | A61B 17/72 606/64 |
| 5,616,142 A | * | 4/1997 | Yuan | A61B 17/8057 606/71 |
| 6,375,684 B1 | * | 4/2002 | Kriek | A61B 17/1666 623/23.39 |
| 6,911,030 B1 | * | 6/2005 | Vanacker | A61B 17/7032 606/270 |
| 8,070,785 B2 | * | 12/2011 | Biscup | A61B 17/686 606/305 |
| 8,486,144 B2 | | 7/2013 | Link | |
| 9,144,506 B2 | * | 9/2015 | Phelps | A61F 2/4455 |
| 9,795,412 B2 | * | 10/2017 | Sinha | A61B 17/68 |
| 2003/0069580 A1 | * | 4/2003 | Langmaid | A61B 17/66 606/59 |
| 2003/0208276 A1 | * | 11/2003 | Berelsman | A61F 2/3804 623/20.11 |
| 2004/0193268 A1 | | 9/2004 | Hazebrouck | |
| 2005/0107794 A1 | | 5/2005 | Hazebrouck | |
| 2008/0287951 A1 | * | 11/2008 | Stoneburner | A61B 17/7208 606/63 |
| 2015/0142124 A1 | | 5/2015 | Link | |
| 2020/0038189 A1 | * | 2/2020 | Williams | A61F 2/4225 |

FOREIGN PATENT DOCUMENTS

| | | |
|---|---|---|
| JP | 2003-250823 | 9/2003 |
| JP | 2011-136234 A | 7/2011 |
| JP | 2015-515895 | 6/2015 |
| WO | WO 2007/028832 A2 | 3/2007 |
| WO | WO 2010/020429 A1 | 2/2010 |

OTHER PUBLICATIONS

English translation of the International Preliminary Report on Patentability (Chapter I) dated Oct. 10, 2019 in corresponding International Application No. PCT/DE2018/100291.
Office Action dated Nov. 27, 2020 in corresponding Japanese Patent Application No. 2019-549480 and its English Translation.
Office Action dated Feb. 18, 2021 issued in corresponding Indian Patent Application No. 201947043194.
Office Action dated Aug. 3, 2021 issued in corresponding Japanese Patent Application No. 2019-549480 and its English Translation.

\* cited by examiner

CONNECTING SLEEVE FOR ANCHORING SHAFTS OF TWO OPPOSITELY ARRANGED PROSTHESES

CROSS-REFERENCE TO RELATED APPLICATIONS

This application is the National Stage entry under 35 U.S.C. § 371 of International Application No. PCT/DE2018/100291 filed on Mar. 29, 2018, published on Oct. 4, 2018 under Publication Number WO 2018/177481, which claims the benefit of priority under 35 U.S.C. § 119 of European Patent Application Number 17164128.5 filed Mar. 31, 2017, the entireties of which are herein incorporated by reference.

The invention relates to a connecting sleeve for anchoring shafts of two oppositely arranged prostheses, preferably on an elongate bone such as a femur. The reinforcing sleeve comprises two receiving bushes, one for each prosthesis shaft, and, arranged between these receiving bushes, a separable coupling region for a connection that resists shear and rotation.

Elongate bones in particular are often provided with joints at both ends. This applies in particular to the elongate bones of the main extremities, for example the femur or humerus. As a consequence of disease or wear, a situation may arise in which artificial joints, joint endoprostheses, are implanted at one end or both ends. In many cases, this is done at one end of the bone first, and at the other end at the same time, at a later time or not at all.

There are cases in which, as a consequence of disease, in particular of bone defects, the elongate bone is too greatly weakened to support joint endoprostheses at its ends. It has moreover been found that complications can arise even after the implantation of a second joint endoprosthesis at the other end. These complications can in particular arise from the fact that the anchoring shafts inserted into the elongate bone, in this case from both ends, reinforce the bone in the respective end regions (namely where the shafts are inserted), but not in the intermediate region in which neither of the two anchoring shafts is located. This region, even if biologically healthy in itself, is therefore relatively weakened by comparison with the end regions that are reinforced by the anchoring shafts. In medical practice, it has been found that bone fractures may occur as a consequence of the uneven distribution of force and of the resulting local increase in loading.

A reinforcing implant is known which has, at each of its ends, a receiving bush for the shaft of a joint endoprosthesis and, arranged between these, a rigid coupling piece (WO 2013/167655 A1). The coupling piece is designed as a wedge action connector. The latter has two wedge pieces which are arranged symmetrically but extend in opposite directions and whose tips each engage in pocket-like recesses on the respective other receiving bush. A separable coupling is thus obtained which, in the closed state, has good force transmission and a high degree of operational reliability. Against this, however, is the disadvantage that such a wedge action connector requires a high degree of manufacturing precision in order to achieve the desired high degree of fastening reliability. Moreover, the production of the pocket-like recesses is extremely complex but is important for the desired securing against rotation. All of this places limits on a broader use and on a reduction in size, for example for use on the humerus.

The object of the invention is to make available an improved reinforcing implant which is less complex and is better suited for a smaller configuration.

The solution according to the invention lies in the features of the independent claim. Advantageous developments form the subject matter of the dependent claims.

In a reinforcing sleeve for anchoring shafts of two oppositely arranged prostheses, preferably on an elongate bone such as a femur, comprising a first receiving bush for one of the prosthesis shafts at one end of the reinforcing sleeve and a second receiving bush for a second of the prosthesis shafts at an opposite end of the reinforcing sleeve, and a separable coupling region that is arranged between them and is connectable in such a way as to resist shear and rotation, provision is made according to the invention that the receiving bushes, at their side directed toward the coupling region, each have a fork of a pair of forks that interact with each other, wherein each fork comprises fork tines and a fork base, and a fitting block is arranged at a foot of the fork (fork base), the side faces of which fitting block are at a distance from each other corresponding to an inner width of the fork, and the side faces are designed to bear on flanks of the fork in a planar manner, wherein at least one fastening screw is arranged transversely through the fork.

The invention is based on the recognition that a fork structure for the coupling is easier to produce than the known wedge connection and yet still satisfies the requirements as regards force transmission and operational reliability. In particular, the critical securing against undesired rotation, i.e. the torsional strength, is satisfied by the fork construction according to the invention, and with noticeably less effort. The invention makes use of the fact that, unlike a wedge connection as known from the prior art, the fork construction does not require an exact fit. A clearance fit between the fork and the fitting block is sufficient in principle, wherein excessive play is eliminated by the fastening screws. The invention thus provides an elegant way of achieving a combination of good force-transmitting properties and greater torsional strength, with fewer demands on the manufacturing tolerances. This is without example in the prior art.

A number of terms used are explained below:

A fork is understood as a structure having at least two elongate, parallel tine-like projections which are arranged in the manner of a U and have between them a fork base. Here, the fork base can also be formed by another component, for example a block, which, if appropriate, can also be configured in one piece with the fork.

According to the invention, a force bridge is formed with little effort between the two anchoring shafts of the prostheses, without this depending on the state of the bone in the intermediate region. The force bridge is completely sufficient in functional terms, such that the bone can, if appropriate, be resected in the intermediate region. The invention is therefore also suitable in particular for the treatment of thin bones, for example the humerus.

In the fitting block, a receiving bore for the fastening screw is expediently provided transversely with respect to the direction of extent of the fork, preferably on both receiving bushes. By means of this arrangement of the receiving bore, the fastening screw permits, on the one hand, a securing of the coupling configured according to the invention as a fork, and, on the other hand, an expedient reduction of play. This applies in particular when the receiving bore is provided on both receiving bushes in the respective fitting block. Preferably, each fork is provided with its own fastening screw.

The lateral sides of the fitting block are preferably designed complementing the fork flanks. The lateral sides thus function as fitting surfaces for the fork, such that a planar contact is obtained that favors the transmission of force. Not only is this advantageous generally for the transmission of force, it also increases the protection against undesired rotation, i.e. increases the torsional strength. Here, the distance between the lateral sides is advantageously chosen such that it corresponds to the distance between the fork tines.

The lateral sides of the fitting block are preferably inclined toward each other, specifically in such a way that they have a smaller spacing in the direction of the fork, i.e. in the direction in which the fork tines point. Seen in cross section, the lateral sides thus have a conical profile which, on the one hand, makes assembly easier and, on the other hand, promotes freedom of play. Here, the fork surfaces are advantageously inclined in a complementary manner to the lateral sides, preferably by the same angle as the lateral sides. In this way, the angles agree over the entire surface, which is optimal for high force transmission and torsional strength.

The receiving bore on the fitting block is expediently configured such that it forms a clearance fit with the fastening screw. The clearance fit does not afford the advantage that is can be produced more easily and with less outlay, it also affords the advantage that it is suitable for compensating certain inaccuracies. In this way, by tightening the fastening screw, it is possible to compensate for dimensional deviations, whether caused by tolerances on the fork or on the fitting block or occurring for other reasons.

According to a particularly advantageous aspect of the invention, possibly meriting independent protection, the distance from the receiving bore in the fork to the fork base is greater than the distance from the receiving bore in the fitting block to the fork base. This is based on the recognition that, when they are inserted into each other, the two forks, upon engagement on the respectively oppositely arranged fitting block, thus reach their end position before the fork base bears on the respectively opposite fitting block. This ensures that the force transmission takes place via the lateral sides on the fitting block. It is thus possible to prevent a dual force transmission path via which the force could act in parallel directly on the fitting block via the fork base; this is a great advantage, since statically indeterminate conditions can thus be safely avoided.

The fork and/or the fitting block of the two receiving bushes are expediently configured symmetrically to each other. This simplifies production and use since, in the best possible scenario, identical parts can be used on both sides. A mix-up is thus ruled out.

The width of the fork is preferably of a greater dimension than the width of the prosthesis shaft that is to be received. In this way, favorable force transmission conditions are achieved. The moments acting on the fork tines are thus somewhat less than the moments acting on the anchoring shaft itself. The danger of overloading of the coupling region with the fork is thus counteracted in a simple but effective way.

The width in the coupling region is preferably greater than the width in the region of the receiving bush. This takes account of the fact that, in the critical coupling region, a slightly increased width affords the advantage of permitting better support of moments, which is favorable for buckling strength and torsional strength. The overall arrangement thus remains comparatively compact, such that it is still suitable for implantation in rather thin and long bones, for example the humerus. The width is expediently oriented on the basis of the bone diameter, preferably approximately the same size or up to 10 to 20% smaller or larger.

The fork and the fitting block are expediently configured in one piece. This affords the advantage of simpler production, and the possibility of achieving smaller dimensions for the overall arrangement.

The invention is explained in more detail below on the basis of an illustrative embodiment and by reference to the attached drawing, in which.

Figure 1:
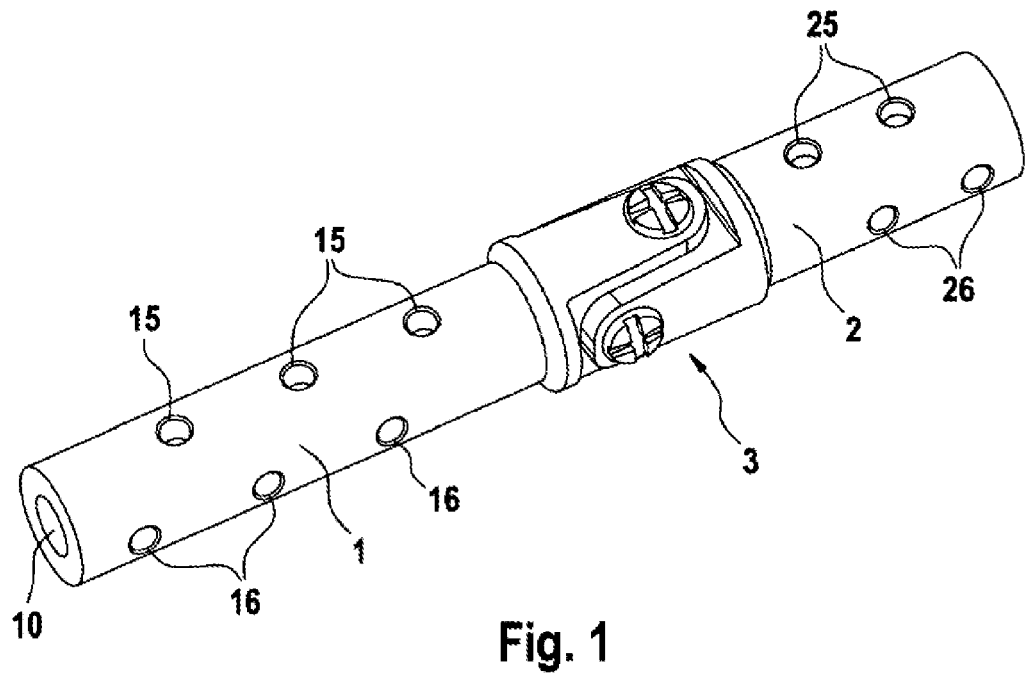
FIG. 1 shows a perspective view of an illustrative embodiment for a connecting sleeve.

An illustrative embodiment of the connecting sleeve according to the invention is described below. It comprises a receiving bush 1, 2 at each of its two ends and, between these, a coupling region 3. Here, the receiving bush designated by reference number 1 is assigned to a distal side, while the receiving bush designated by reference number 2 is assigned to a proximal side.

The receiving bushes 1, 2 are of substantially the same configuration. They differ only in terms of having a different length and a different width of the respective receiving bore. The explanation is given by way of example on the basis of the distally arranged receiving bush 1. It is of a substantially hollow cylindrical shape with a smooth jacket surface and is preferably produced from a biocompatible material, in particular a metal such as titanium or cobalt-chromium-molybdenum (CoCrMo). The external diameter is adapted to the width of the bone on which the implantation is provided. In most cases, the external diameter is generally chosen such that it approximately corresponds to the diameter of the possibly resected bone. This means that the chosen external diameter is not greater than one corresponding to the width of the bone. In the present illustrative embodiment, the connecting sleeve is provided for implantation in a humerus 9.

Figure 2:
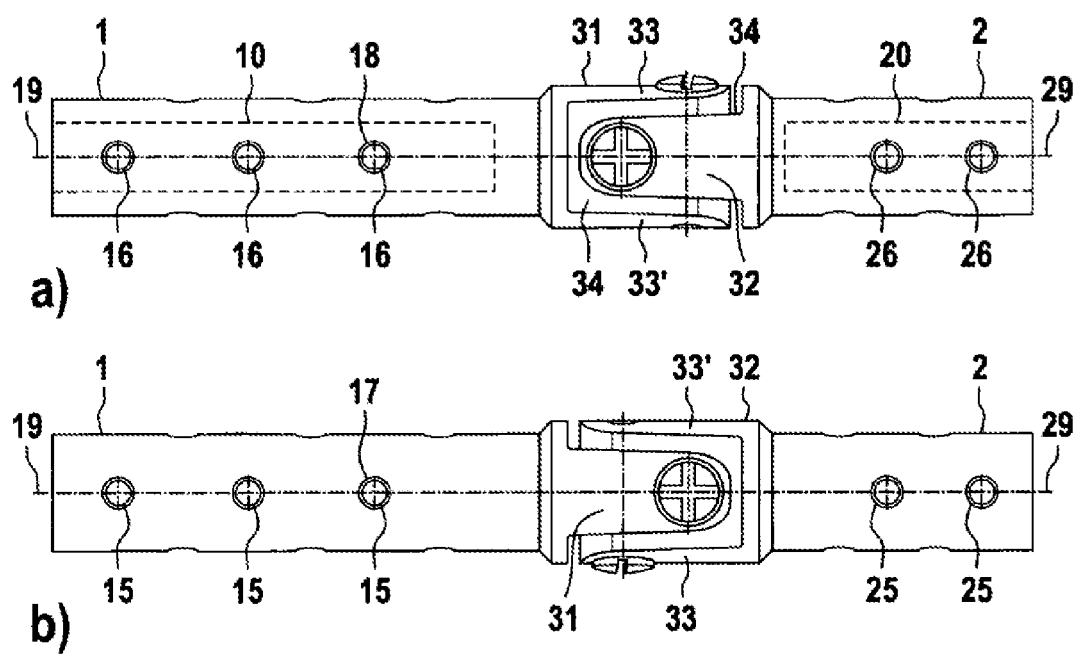
FIG. 2 shows a plan view (FIG. 2a) and a side view (FIG. 2b) of the illustrative embodiment shown in FIG. 1.

In its interior, the receiving bush 1 has a cavity 10 extending in an axial direction. This cavity 10 is configured as a cylindrical bore but can also be differently shaped (conical, stepped bore, etc.). The cavity 10 opens out on an outer end face of the receiving bush 1. Pairs of rows of holes are provided opposite each other in the jacket of the receiving bush 1. A plurality of holes 15 are arranged on a front face and rear face (see FIG. 2b), while a plurality of holes 16, offset from these in the axial direction, are arranged on the two lateral sides (see FIG. 2a). The offset between the holes 15 and 16 is chosen here such that the rows of holes are offset from each other by approximately half a hole spacing. This is illustrated in FIG. 1.

Figure 3:
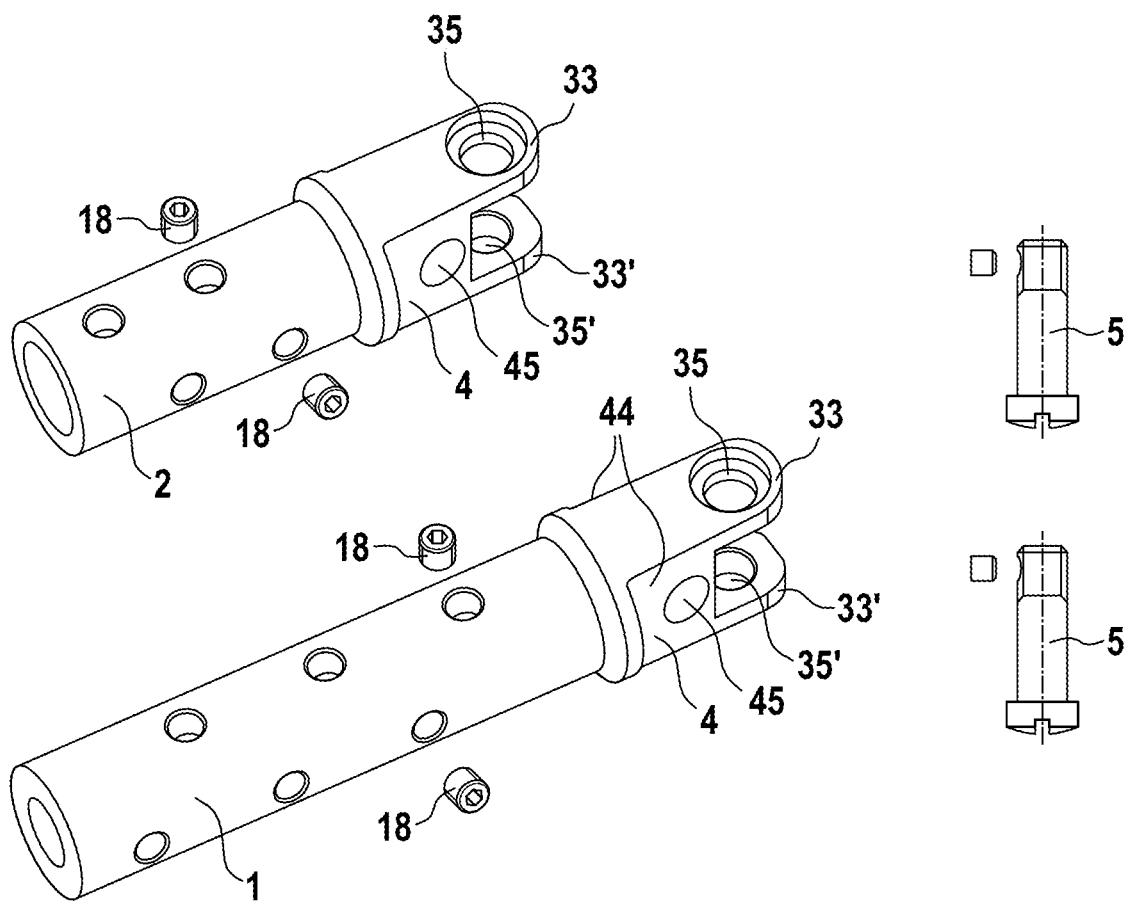
FIG. 3 shows a view of the individual parts of the connecting sleeve according to the first illustrative embodiment.

The receiving holes 15, 16 are moreover oriented such that they point to the center axis 19 of the interior 10. They serve to receive fastening screws for fixing an anchoring shaft of an endoprosthesis pushed into the receiving space 10. For this purpose, the receiving holes 15, 16 are each provided with a thread 17, 18 for receiving a fastening screw 18 configured as a grub screw (see FIG. 3).

The proximal receiving bush 2 is shaped correspondingly, with a cavity 20, holes 25, 26 and a center axis 29. To avoid repetition, reference is made to the above observations concerning the receiving bush 1, which observations apply analogously here. In the illustrative embodiment shown, the receiving bush 2 is slightly shorter than the receiving bush 1.

The coupling region 3 is located at that end of the proximal and distal receiving bush 1, 2 lying opposite the respective front end. Arranged on each of the two receiving bushes 1, 2 is a respective fork 31, 32, each of which has two diametrically opposite fork tines 33, 33'. The two fork tines 33, 33' are configured with mirror symmetry. At their end, they each have openings 35, 35' which are flush with each other and which serve to receive a fastening screw 5. For this purpose, the opening 35' has an inner thread, which is designed interacting with an outer thread on the shank of the fastening screw 5. The opening 35 is designed as a through-hole and has a countersink for receiving a head of the fastening screw 5.

The two fork tines 33, 33' are arranged in a U shape, with a fork base 34 lying between them. A fitting block 4 is provided in each case on the fork base 34. As in the illustrative embodiment shown, this fitting block 4 can be configured in one piece with the respective fork 31, 32. Each of the two fitting blocks 4 has a receiving bore 45, which is formed transversely with respect to the longitudinal axis 19, 29 of the respective receiving bush 1, 2. It serves to receive the shaft of the fastening screw 5. The diameter of the receiving bore 43 is chosen such that a clearance fit is obtained with the shaft of the fastening screw 5. A PE pin 51 for securing the screw can be received at the thread region of each fastening screw 5.

The fitting block 4 has two mutually opposite lateral sides 44 at which receiving bore 45 begins or ends. The distance between the lateral sides 44 corresponds to the distance between the two fork tines 33, 33'. The lateral sides 44 are preferably oriented slightly obliquely to each other, such that they have a slightly greater spacing from each other at their side directed toward the receiving bore 10, 20 than at their side directed toward the fork tines 33, 33'. The enclosed angle α expediently measures approximately 5°.

Accordingly, the fork tines 33, 33' are likewise slightly widened conically on their inner face. This means that, at their outer free end, they have a slightly greater spacing than they do in the direction toward the fork base 34 with the fitting block 4. For this purpose, it is likewise preferable to choose an enclosed angle β which corresponds to the angle α of the fitting surfaces 44. Since these angles correspond, the inner faces of the fork tines 33, 33' bear on the lateral sides 44 of the fitting block 4 with planar contact in a way that is advantageous for force transmission. Moreover, certain tolerance deviations are compensated by the angles, such that a reliable force-fit connection is obtained even if manufacture is not absolutely exact.

The assembling is carried out as follows: the two forks 31, 32 are placed in a position facing each other, wherein one fork 31 is rotated 90° with respect to the other fork 32 (see FIG. 4). The two receiving bushes 1, 2 with their forks 31, 32 are then moved toward each other until they engage in each other (see FIG. 1). The fork tines 33, 33' of one fork 31 comes to bear on the lateral faces 44 of the fitting block 4 of the opposite fork 32, and vice versa. In this way, the openings 35, 35' of each of the two forks 31, 32 are flush with the receiving bore 45 of the fitting block 4 on the respective other fork 32, 31. One of the fastening screws 5 is then inserted through the openings 35, 35' and the receiving bore 45 and is tightened. By means of the tightening, and in conjunction with the conical shape of the inner faces of the fork 31, 32, the two receiving bushes 1, 2 are safely fixed relative to each other in a way that compensates for play and that is not sensitive to tolerances. A rigid and rotationally fixed transmission of force between the two receiving bushes 1, 2 is thus achieved.

Figure 4:
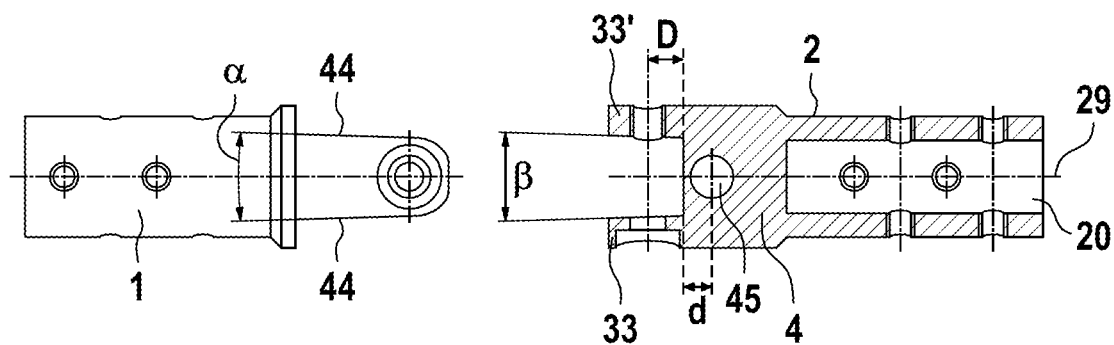
FIG. 4 shows an enlarged detail depicting a coupling region with fork and fitting block.

Reference is now made to FIG. 4. There, the letter d designates the dimension for the spacing of the hole center of the receiving bore 45 in the fitting block 4. Moreover, the corresponding dimension for the spacing of the hole center of the openings 35, 35' on the fork tines 33, 33' is designated by the dimension D. The dimensions are advantageously chosen such that the dimension D is not equal to the dimension d, but slightly larger. This ensures that the connection between the forks 31 and 32 is effected via the fastening screws 5, and the force is not conveyed in a statically indeterminate manner via the front face of the fitting blocks 4. In this way, the non-sensitivity to tolerance deviations is increased further.

Figure 5:
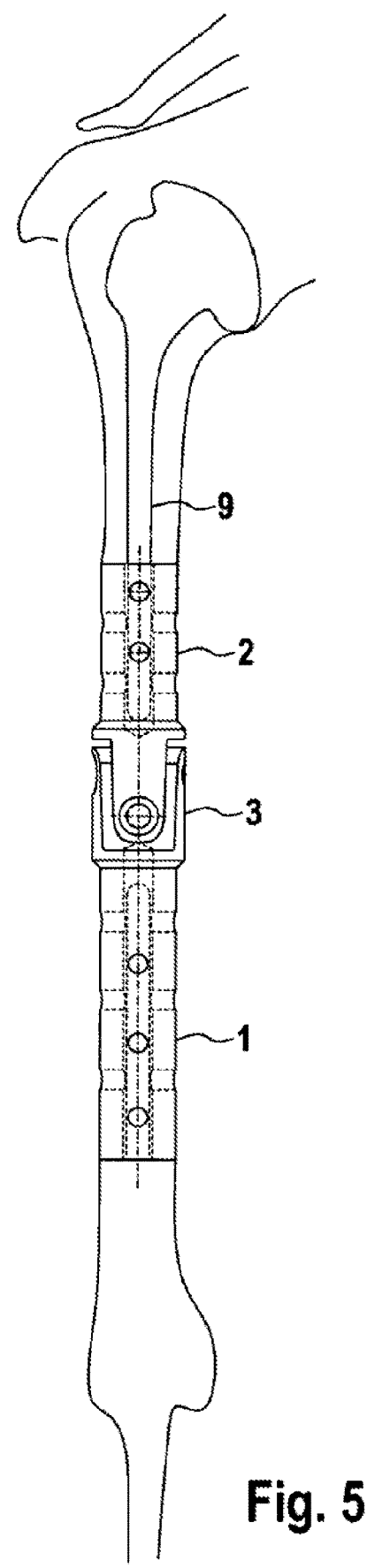
FIG. 5 shows a view with the connecting sleeve in the stated implanted in the humerus.

FIG. 5 shows the connecting sleeve in the state when implanted in a humerus 9. The figure depicts the distally arranged receiving bush 1, the proximally arranged receiving bush 2, and the coupling region 3 between them. The width in the region of the coupling region 3 is slightly greater than the width of the receiving bushes 1, 2. In the illustrative embodiment shown, the width is approximately 10% greater. In this way, improved fastening of the two receiving bushes 1, relative to each other is achieved, while the widening in the critical coupling region 3 between the two receiving bushes 1, 2 is negligible in practice and is physiologically well tolerated.

The invention claimed is:

1. A connecting sleeve for anchoring shafts of two oppositely arranged prostheses on an elongate bone, comprising a first receiving bush configured for receiving a shaft of one of the prosthesis at one end of the connecting sleeve and a second receiving bush configured for receiving a shaft of the other prosthesis at an opposite end of the connecting sleeve, and a separable coupling region that is arranged between said first receiving bush and said second receiving bush and is connectable in such a way as to resist shear and rotation, wherein: the receiving bushes, at their side directed toward the coupling region, each have a fork that interact with each other, wherein each fork comprises fork tines and a fork base, flanks of the forks being inward facing surfaces of each fork tine; and a fitting block is arranged at the base of each fork between the fork tines of each fork, the lateral sides of each either fitting block are at a distance from each other corresponding to an inner width of the interacting forks, and wherein in a mounted state the flanks of either fork of the interacting forks are bearing in a planar manner on lateral sides of the fitting block of the other fork of the interacting forks, and wherein at least one fastening screw is arranged transversely through each fork, wherein, in each fitting block, a receiving bore for the fastening screw is provided transversely with respect to the direction of extent of each fork, and the lateral sides of each fitting block are inclined toward each other, with the smaller spacing in the direction of the fork tines of the respective fork comprising each fitting block, wherein the fork flanks are inclined in a complementary manner, and the distance from a receiving opening in at least one of the forks to the respective fork base is greater than the distance from the receiving bore in the fitting block to said respective fork base.

2. The connecting sleeve as claimed in claim 1, wherein the lateral sides of each of the fitting blocks are designed as fitting surfaces complementing the fork flanks.

3. The connecting sleeve as claimed in claim 2, wherein the distance between the lateral sides corresponds to the distance between the fork tines.

4. The connecting sleeve as claimed in claim 2, wherein the receiving bore on each fitting block forms a clearance fit with the fastening screw.

5. The connecting sleeve as claimed in claim 1, wherein either of the forks of the two receiving bushes are configured symmetrically to each other, and the fitting blocks of the two receiving bushes are configured symmetrically to each other.

6. The connecting sleeve as claimed in claim 1, wherein the width of at least one of the forks is of a greater dimension than the width of the prosthesis shaft that is to be received.

7. The connecting sleeve as claimed in claim 1, wherein the width in the coupling region is greater than the width in the region of the receiving bushes, but greater by no more than a quarter.

8. The connecting sleeve as claimed in claim 7, wherein the width in the coupling region is greater than the width in the region of the receiving bushes, but greater by no more than a tenth.

9. The connecting sleeve as claimed in claim 1, wherein, with respect to at least one of the receiving bushes, the fork and the fitting block arranged at the fork base of said fork are configured in one piece.

10. The connecting sleeve as claimed in claim 1, wherein each fork is provided with its own fastening screw.

* * * * *